(12) United States Patent
Guo et al.

(10) Patent No.: US 9,405,023 B2
(45) Date of Patent: Aug. 2, 2016

(54) METHOD AND APPARATUS FOR INTERFACING WITH AN ARRAY OF PHOTODETECTORS

(71) Applicant: General Electric Company, Schenectady, NY (US)

(72) Inventors: Jianjun Guo, Ballston Spa, NY (US); Sergei Ivanovich Dolinsky, Clifton Park, NY (US); Changlyong Kim, Brookfield, WI (US); James Lindgren Malaney, Waukesha, WI (US); David Leo McDaniel, Dousman, WI (US); William Peterson, Sussex, WI (US)

(73) Assignee: General Electric Company, Niskayuna, NY (US)

( * ) Notice: Subject to any disclaimer, the term of this patent is extended or adjusted under 35 U.S.C. 154(b) by 553 days.

(21) Appl. No.: 13/764,960

(22) Filed: Feb. 12, 2013

(65) Prior Publication Data

US 2014/0224963 A1 Aug. 14, 2014

(51) Int. Cl.
*H01J 40/14* (2006.01)
*H01L 27/00* (2006.01)
*G01T 1/29* (2006.01)
*G01T 1/16* (2006.01)
(Continued)

(52) U.S. Cl.
CPC .............. *G01T 1/2985* (2013.01); *A61B 6/037* (2013.01); *G01T 1/1603* (2013.01); *G01T 1/1647* (2013.01); *G01R 33/481* (2013.01)

(58) Field of Classification Search
CPC ............. G01T 1/24; G01T 1/42; G01T 1/164; G01T 1/2985; G01V 3/00; Y10S 378/901; Y10S 378/00

USPC ................ 250/208.1, 370.01, 214 R, 363.03, 250/214 A, 363.01, 363.02, 363.04, 363.05, 250/214.1, 370.08, 370.09, 370.1, 370.11; 327/51, 69, 70; 378/1, 4–27
See application file for complete search history.

(56) References Cited

U.S. PATENT DOCUMENTS 8,068,896 B2 11/2011 Daghighian et al.
8,110,806 B2 2/2012 Burr et al.
(Continued)

OTHER PUBLICATIONS

Deng et al. "Development of an Eight-Channel Time-Based Readout ASIC for PET Applications", IEEE Transactions on Nuclear Science, vol. 58 (6), Dec. 2011, pp. 3212-3218.*

(Continued)

Primary Examiner — Pascal M Bui Pho
(74) Attorney, Agent, or Firm — Robert M. McCarthy (57) ABSTRACT

A multichannel application specific integrated circuit (ASIC) for interfacing with an array of photodetectors in a positron emission tomography (PET) imaging system includes a front end circuit configured to be coupled to the photodetectors and to receive discrete analog signals therefrom. The ASIC further includes a time discriminating circuit operably coupled to the front end circuit and configured to generate a hit signal based on a combination of the discrete analog signals, and an energy discriminating circuit operably coupled to the front end circuit and configured to generate a summed energy output signal based on each of the discrete analog signals and summed row and column output signals based on each of the discrete analog signals. The summed energy output signal represents an energy level of the detected radiation in the array of photodetectors, and the summed row and column output signals represent a location of the detected radiation.

17 Claims, 5 Drawing Sheets

(51) Int. Cl.
*G01T 1/164* (2006.01)
*A61B 6/03* (2006.01)
*G01R 33/48* (2006.01)

(56) References Cited

U.S. PATENT DOCUMENTS

| | | | |
|---|---|---|---|
| 2005/0116139 A1* | 6/2005 | Mikkelsen | H04N 3/1562 250/208.1 |
| 2005/0167599 A1* | 8/2005 | Schlyer et al. | 250/363.03 |
| 2008/0284428 A1* | 11/2008 | Fiedler et al. | 324/307 |
| 2010/0316184 A1 | 12/2010 | Iwanczyk et al. | |
| 2011/0001053 A1* | 1/2011 | Solf | 250/370.08 |
| 2011/0215248 A1 | 9/2011 | Lewellen et al. | |

OTHER PUBLICATIONS

Marzocca et al. "Design and characterization of a 32-channel front-end ASIC for Silicon Photo-Multiplier detectors", Advances in Sensors and Interfaces (IWASI), 2011 4th IEEE International Workshop on, Jun. 28-29, 2011, Savelletri di Fasano, Italy, pp. 212-217.*

Janecek et al., "A High-Speed Multi-Channel Readout for SSPM Arrays", IEEE Transactions on Nuclear Science, vol. 59, Issue 1, pp. 13-18, Feb. 2012.

Deng et al., "Development of an Eight-Channel Time-Based Readout ASIC for PET Applications", IEEE Transactions on Nuclear Science, vol. 58, Issue 6, pp. 3212-3218, Dec. 2011.

Fang et al., "Design of a Multi-Channel Front-End Readout ASIC with Low Noise and Large Dynamic Input Range for APD-Based PET Imaging", IEEE Transactions on Nuclear Science, vol. 57, Issue 3, pp. 1015-1022, Jun. 2010.

Corsi et al., "Front-end Electronics for Silicon Photo-Multipliers Coupled to Fast Scintillators", 2010 IEEE Nuclear Science Symposium Conference Record (NSS/MIC), pp. 1332-1339, Oct.-Nov. 2010, Location: Knoxville, Tennessee.

Callier et al., "Silicon Photomultiplier Integrated Readout Chip (SPIROC) for the Ilc: Measurements and Possible Further Development", 2009 IEEE Nuclear Science Symposium Conference Record (NSS/MIC), pp. 42-46, Oct.-Nov. 2009, Location: Orlando, Florida.

Corsi et al., "Preliminary Results from a Current Mode CMOS Front-End Circuit for Silicon Photomultiplier Detectors", 2007 IEEE Nuclear Science Symposium Conference Record, pp. 360-365, Oct.-Nov. 2007, Location: Honolulu, Hawaii.

* cited by examiner

METHOD AND APPARATUS FOR INTERFACING WITH AN ARRAY OF PHOTODETECTORS

FIELD

This disclosure relates generally to imaging, and more particularly, to apparatus and methods of processing analog signals generated by solid state photomultiplier devices.

BACKGROUND

A silicon photomultiplier (SiPM) is an array of passively quenched Geiger-mode avalanche photodiodes (APD) for detecting impinging photons. SiPM can provide information about certain parameters, such as the time of the impingement event, the energy associated with the event, and the position of the event within the detector. These parameters can be determined through processing algorithms applied to the analog signals generated by the SiPM. Some conventional SiPMs can produce very fast signals, which provides a high degree of timing accuracy.

SiPMs provide certain advantages over conventional photomultiplier tubes (PMTs), and are therefore being used in many applications, including Positron Emission Tomography (PET) for medical imaging. These advantages include better photon detection efficiency (i.e., a high probability of detecting an impinging photon), compactness, ruggedness, low operational voltage, insensitivity to magnetic fields and low cost.

However, the transmission of analog signals from the SiPM for processing can present problems. For example, due to its small size, many SiPMs often are used in a given application. Therefore, many individual signal lines may be required to carry the signals, which increases complexity in readout electronics, manufacturing complexity and cost. Furthermore, the quality of the signal is more likely to deteriorate as the size and complexity of the SiPM increases.

SUMMARY

In an embodiment, a multichannel application specific integrated circuit (ASIC) for interfacing with an array of photodetectors in a positron emission tomography (PET) imaging system includes a front end circuit configured to be coupled to the array of photodetectors and to receive a plurality of discrete analog signals therefrom. The ASIC further includes a time discriminating circuit operably coupled to the front end circuit and configured to generate a hit signal based on a combination of the discrete analog signals. The hit signal represents an indication that radiation has been detected by the array of photodetectors. The ASIC further includes an energy discriminating circuit operably coupled to the front end circuit and configured to generate a summed energy output signal based on each of the discrete analog signals and summed row and column output signals based on each of the discrete analog signals. The summed energy output signal represents an energy level of the detected radiation, and the summed row and column output signals represent a location of the detected radiation in the array of photodetectors.

In some embodiments, the ASIC may further include a first channel operably coupled between the front end circuit and the time discriminating circuit, and a plurality of second channels each operably coupled between the front end circuit and the energy discriminating circuit. In some embodiments, the front end circuit may be further configured to transfer the combination of discrete analog signals to the time discriminating circuit using the first channel, and transfer each of the discrete analog signals to the energy discriminating circuit using corresponding ones of the plurality of second channels.

In some embodiments, the front end circuit may further include a front end input operably coupled to an anode of one photodetector in the array of photodetectors, a current mirror, and a feedback network operably coupled to the front end input and the current mirror. The front end circuit may further include an amplifier having an inverting input operably coupled to the front end input, a non-inverting input operably coupled to a bias voltage, and an output. The front end circuit may further include a transistor having a source operably coupled to the front end input, a sink operably coupled to the current mirror, and a gate operably coupled to the output of the amplifier. The front end circuit may further include a first front end output operably coupled to the current mirror and to the first channel, and a second front end output operably coupled a corresponding one of the plurality of second channels. In some embodiments, the front end circuit may be further configured to enable and disable individual photodetectors in the array using a plurality of bias voltages. In some embodiments, the ASIC may further include a biasing circuit operably coupled to the front end circuit and configured to generate the plurality of bias voltages. In some embodiments, the biasing circuit may include a multichannel digital-to-analog converter.

In some embodiments, the front end circuit may be coupled to an anode of each photodetector in the array of photodetectors. In some embodiments, the ASIC may further include a controller operably coupled to the front end circuit and configured to enable and disable individual photodetectors in the array via the front end circuit. In some embodiments, the array of photodiodes may include an array of Geiger-mode avalanche photodiodes.

According to an embodiment, a method of interfacing with an array of photodetectors in a positron emission tomography (PET) imaging system includes receiving discrete analog signals from each photodetector in the array of photodetectors using a front end circuit and generating a hit signal based on a combination of the discrete analog signals using a time discriminating circuit operably coupled to the front end circuit. The hit signal represents an indication that radiation has been detected by the array of photodetectors. The method further includes generating a summed energy output signal based on each of the discrete analog signals using an energy discriminating circuit operably coupled to the front end circuit. The summed energy output signal represents an energy level of the detected radiation. The method further includes generating summed row and column output signals based on each of the discrete analog signals using the energy discriminating circuit. The summed row and column output signals represent a location of the detected radiation in the array of photodetectors.

In some embodiments, the method may further include transferring the combination of discrete analog signals from the front end circuit to the time discriminating circuit using a first channel operably coupled between the front end circuit and the time discriminating circuit, and transferring each of the discrete analog signals from the front end circuit to the energy discriminating circuit using corresponding ones of a plurality of second channels each operably coupled between the front end circuit and the energy discriminating circuit.

In some embodiments, the method may further include enabling and disabling individual photodetectors in the array using at least one of a plurality of bias voltages each corresponding to a respective photodetector. In some embodiments, the method may further include generating the plurality of bias voltages using a biasing circuit operably coupled to the front end circuit.

According to an embodiment, a multichannel application specific integrated circuit for interfacing with an array of photodetectors in a positron emission tomography imaging system includes a plurality of inputs each configured to be coupled to the array of photodetectors and to receive a plurality of discrete analog signals from each photodetector in the array and a time discriminating circuit configured to generate a hit signal based on a combination of the discrete analog signals. The hit signal represents an indication that radiation has been detected by the array of photodetectors. The ASIC further includes an energy discriminating circuit configured to generate a summed energy output signal based on each of the discrete analog signals and summed row and column output signals based on each of the discrete analog signals. The summed energy output signal represents an energy level of the detected radiation, and the summed row and column output signals represent a location of the detected radiation in the array of photodetectors. The ASIC further includes means for transferring the discrete analog signals from the plurality of inputs to the time discriminating circuit and to the energy discriminating circuit.

In some embodiments, the means for transferring the discrete analog signals may include a plurality of amplifiers. In some embodiments, the means for transferring the discrete analog signals may further include a first channel operably coupled between the plurality of inputs and the time discriminating circuit, and a plurality of second channels each operably coupled between the plurality of inputs and the energy discriminating circuit. Each of the plurality of amplifiers may include an input operably coupled to an anode of one photodetector in the array of photodetectors, a first output operably coupled to the first channel, and a second output operably coupled to a corresponding one of the plurality of second channels. In some embodiments, the means for transferring the discrete analog signals may include a plurality of current mirrors. In some embodiments, the ASIC may further include means for enabling and disabling individual photodetectors in the array. In some embodiments, the means for enabling and disabling individual photodetectors in the array may include a biasing circuit configured to generate a plurality of bias voltages.

BRIEF DESCRIPTION OF THE DRAWINGS

Features and aspects of embodiments are described below with reference to the accompanying drawings, in which elements are not necessarily depicted to scale.

DETAILED DESCRIPTION

Exemplary embodiments are directed to apparatus and methods of processing analog signals generated by one or more SiPMs. In one embodiment, a multichannel readout front-end application-specific integrated circuit (ASIC) interfaces with an array of SiPMs in a Positron Emission Tomography (PET) system. The ASIC is configured to provide information on the timing, energy, and location of events in each SiPM to a processing system, as well as the ability to bias each SiPM.

Figure 1:
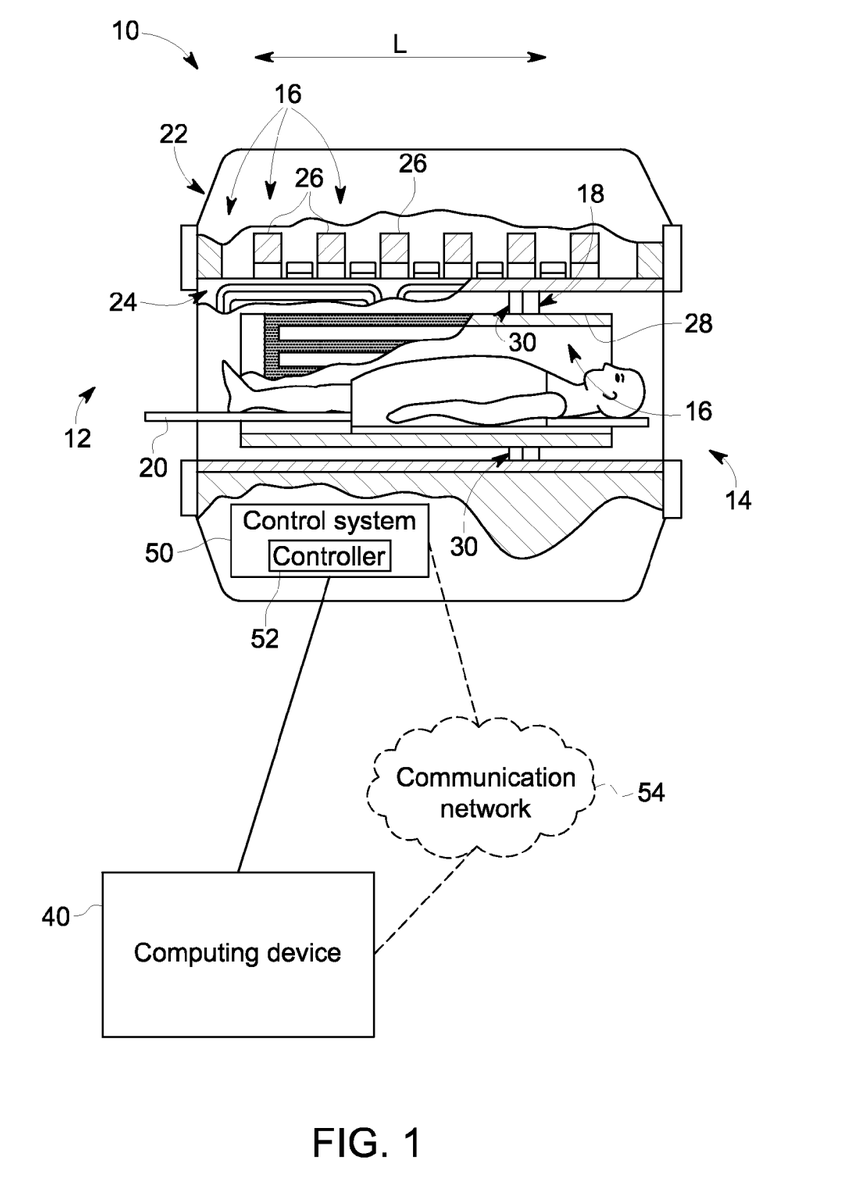
FIG. 1 is a block diagram of one example of a PET-MRI scanner, in accordance with one embodiment.

FIG. 1 depicts one example of a hybrid or combined Positron Emission Tomography (PET)—Magnetic Resonance Imaging (MRI) scanner 10 that can be used in conjunction with various embodiments. The scanner 10 can generally extend longitudinally along a longitudinal axis L from a proximal end 12 to the distal end 14. The scanner 10 can include MRI components 16 forming an MRI scanner portion configured to acquire MR data and/or PET imaging components 18 forming a PET image scanner portion configured to acquire PET image data, and a support structure, e.g., a bed 20 (or table), configured to translate along the longitudinal axis L from the proximal end 12 to the distal end 14 to position the bed 20 with respect to a field of view (FOV) of the MRI scanner portion and a FOV of the PET scanner portion. Although some embodiments described herein include PET-MR embodiments, it will be understood that other embodiments can include PET, PET-CT, PET-MR and/or other gamma ray detectors.

In some embodiments, the MRI components 16 can include a magnet assembly 22 and a gradient coil assembly 24, which can be implemented separately or as part of the magnet assembly 22. The magnet assembly 22 can include a polarizing main magnet 26. The MRI components 16 can include an RF coil assembly 28, which can be implemented as a radio frequency (RF) transmit coil and a phased array receive coil. The RF coil assembly 28 can be configured to transmit RF excitation pulses and to receive MR signals radiating from the subject in response to the RF excitation pulses. The gradient assembly 24 can include one or more physical gradient coils (e.g., three gradient coils having orthogonal axes) to produce magnetic field gradients to spatially encode acquired MR data output from the scanner 10. according to a k-space or raw data matrix.

The PET imaging components 18 of the scanner 10 can include a positron emission detector 30, configured to detect gamma rays from positron annihilations emitted from a subject. Detector 30 can include scintillators and photon detection electronics. The detector 30 can be of any suitable construction and have any suitable arrangement for acquiring PET data. For example, in exemplary embodiments, the detector 30 can have a ring configuration. Gamma ray incidences captured by the scintillators of the detector 30 can be transformed, by the photon detector 30, into electrical signals, which can be conditioned and processed to output digital signals that can match pairs of gamma ray detections as potential coincidence events. When two gamma rays strike detectors approximately opposite one another, it is possible, absent the interactions of randoms and scatters detections, that a positron annihilation took place somewhere along the line between the detectors. The coincidences can be sorted and integrated as PET data that can be processed and/or stored via a computing system 40.

In an exemplary embodiment, the scanner 10 can include a control system 50 having a processing device, e.g., controller 52, for controlling an operation of the scanner 10. The controller 52 of the control system 50 can be programmed and/or configured to control an operation of the MRI components 16, PET components 18, and/or bed 20. While the control system 50 is depicted as being included in the scanner 10, those skilled in the art will recognize that the control system 50, or portions thereof, can be implemented separately and apart from the scanner 10 and can be communicatively coupled to the scanner 10. The control system 50 can be in communication with a computing device 40 such that the scanner 10 can be programmed and/or controlled, via a computing system 40 communicatively coupled to the control system 50 to transmit data and/or commands to the controller 52 of the control system 50 to control an operation of the scanner 10. In some embodiments, the computing device 40 can be in communication with the control system 50 via a communications network 54. In some embodiments, the computing device 40 includes an ASIC, such as ASIC 120 described below with respect to FIG. 2.

In exemplary embodiments, the computing system 40 can configure and/or program the controller 52 of the control system 50 to control the MRI components 16, PET components 18, and/or the bed 20 to perform a scan sequence in response to instructions, commands, and/or requests transmitted to the control system 50 by the computing device 40. As one example, the controller 52 of the control system 50 can be programmed to acquire a sequence of PET images by passing the bed, upon which the subject is supported, through the field of view of the PET scanner portion of the scanner 10. As another example, the controller 52 of the control system can be programmed and/or configured (e.g., via the computing device 40) to generate RF and gradient pulses of a scan sequence for acquisition of MR images.

Gradient pulses can be produced during the MR data acquisition by controlling one or more physical gradient coils in a gradient coil assembly 24 to produce magnetic field gradients to spatially encode acquired MR data output from the scanner 10. MR signals resulting from the excitation pulses, emitted by excited nuclei in a subject, can be sensed by the RF coil assembly 28, and can be provided to the computing system for processing. In some embodiments, PET data and MR data can be concurrently acquired by the scanner 10.

In exemplary embodiments, the field of view (FOV) of the MR data acquisition can be shifted by the control system 50 (e.g., at the direction of the computing device 40). For example, a location of the FOV can be controlled by controlling a frequency of the MR receiver and/or a phase of the MR receiver (e.g., via the computing device 40 and/or control system 50). The FOV defines the imaging area of the MRI scanner portion such that portions of the subject that are within the FOV are imaged by the MRI scanner portion. MR data can be acquired for a subject by shifting the FOV of the MRI scanner portion and/or by adjusting a position of the bed 20 with respect to the FOV. For example, a full/whole-body MR scan of a patient can be accomplished by positioning the bed 20 within the scanner 10 and acquiring MR data for different fields of view and/or by maintaining a static field of view and passing the bed 20, upon which the subject is supported, through the field of view.

The anatomy of the subject can be identified from the MR scout images by generating (via the computing device 40) an anatomy map that includes an outline of the subject's body and the location of major organs such as the lungs. The outline can be generated based on a pixel intensity contrast between the subject's body and the surrounding environment of the subject (e.g., air). The outline generated by the computing device 40 can be used to determine an orientation of the subject on the bed 20 for example by identifying the legs and head of the subject. Using the outline and organ locations, the schedule of PET scans can be generated (via the controller 52 and/or computing device) to segment the scans according to the anatomy and orientation of the subject as well as the height of the subject so that the scheduled scans can integrally cover the subject's anatomy.

Figure 2:
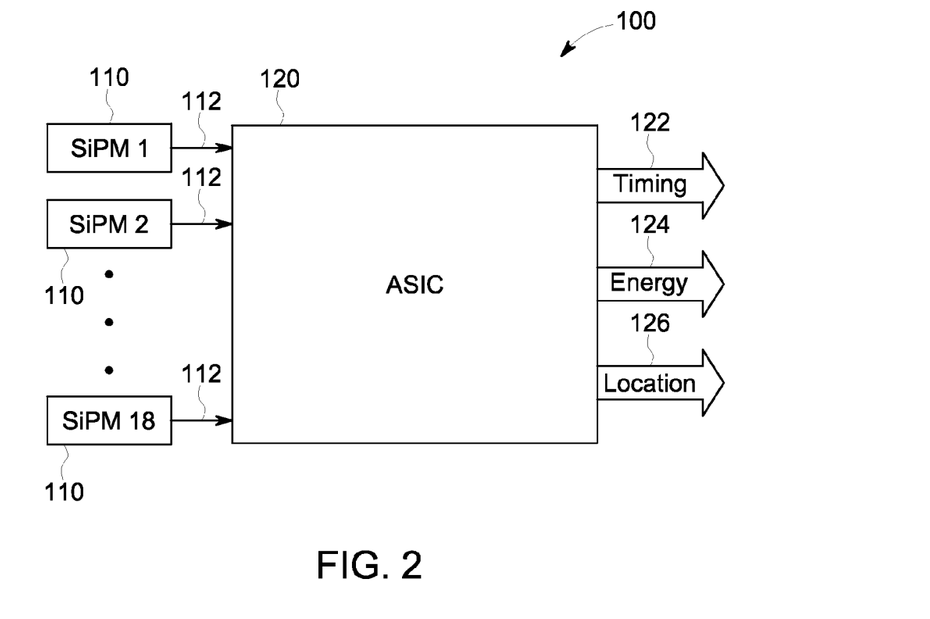
FIG. 2 is a block diagram of one example of a PET data acquisition system, in accordance with one embodiment.

FIG. 2 is a block diagram of one example of a PET data acquisition system 100, according to one embodiment. The system 100 may, for example, be included in the scanner 10 and/or computing device 40 of FIG. 1. The system 100 includes a plurality of SiPMs 110, and an ASIC 120. Each SiPM 110 has an analog anode output 112 in electrical communication with the ASIC 120. When a 511 keV gamma ray interacts with a scintillator, light is generated. This scintillated light is detected by at least one of the SiPMs 110 and rapidly amplified. The anode output 112 can be used as an input to the ASIC 120, such as described below. The ASIC 120 provides, as outputs, one or more timing signals 122, energy signals 124 and/or position signals 126 each representing information obtained by the SiPMs 110 from, for example, a PET scanner (not shown) after processing by the ASIC 120. In an exemplary embodiment, the system 100 can include eighteen (18) SiPMs 110, although it will be understood that in other embodiments different quantities of SiPMs 110 can be used.

Figure 3:
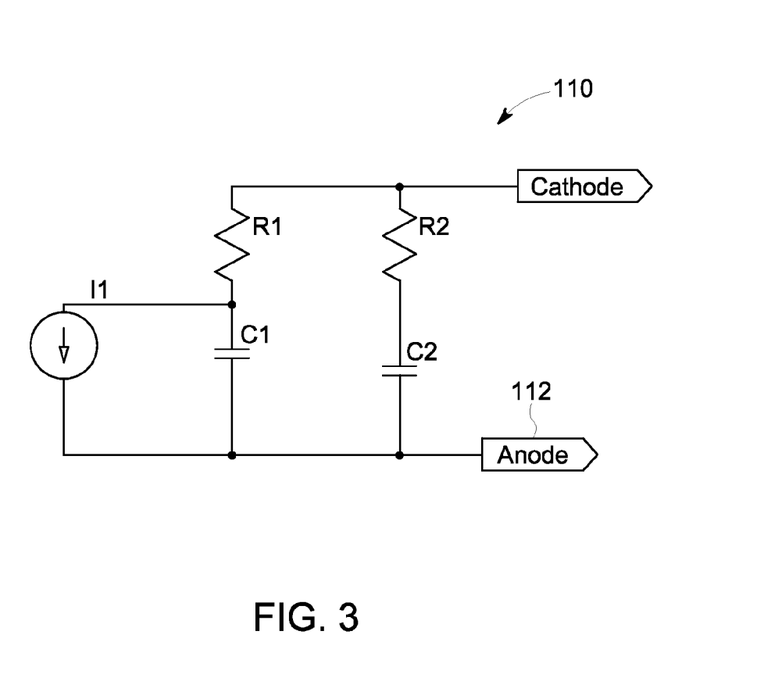
FIG. 3 depicts a schematic of one example of a SiPM circuit, in accordance with one embodiment.
Figure 4:
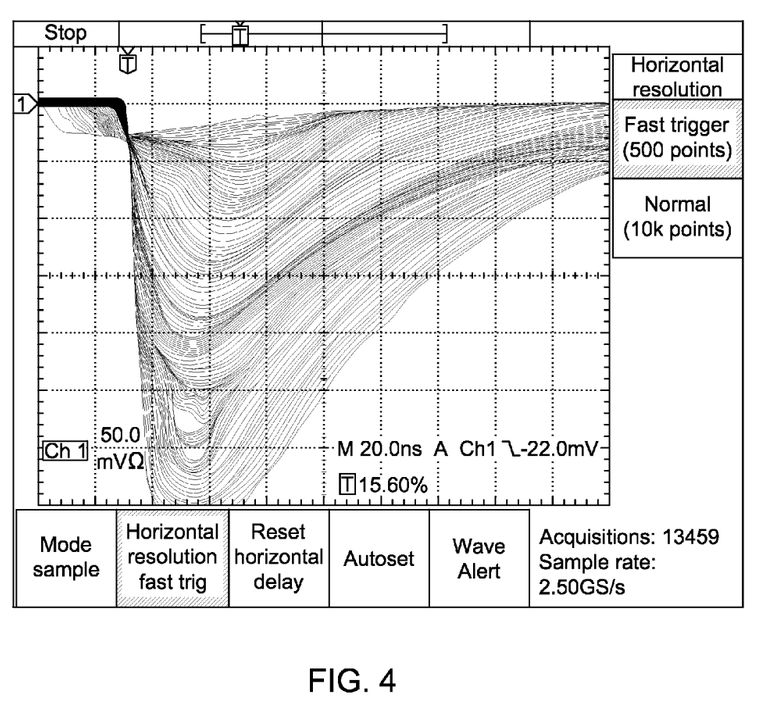
FIG. 4 shows a sample pulse out of the SiPM of FIG. 2.

FIG. 3 depicts an equivalent schematic of one example of a circuit of the SiPM 110 of FIG. 2. The SiPM 110 includes the analog anode output 112. In one embodiment, the anode output 112 of each of the SiPMs 110 can be used as an input to the ASIC. FIG. 4 shows a sample pulse out of a single SiPM 110 after amplification. The predominate trace in FIG. 4 represents a 511 keV gamma signal.

Figure 5:
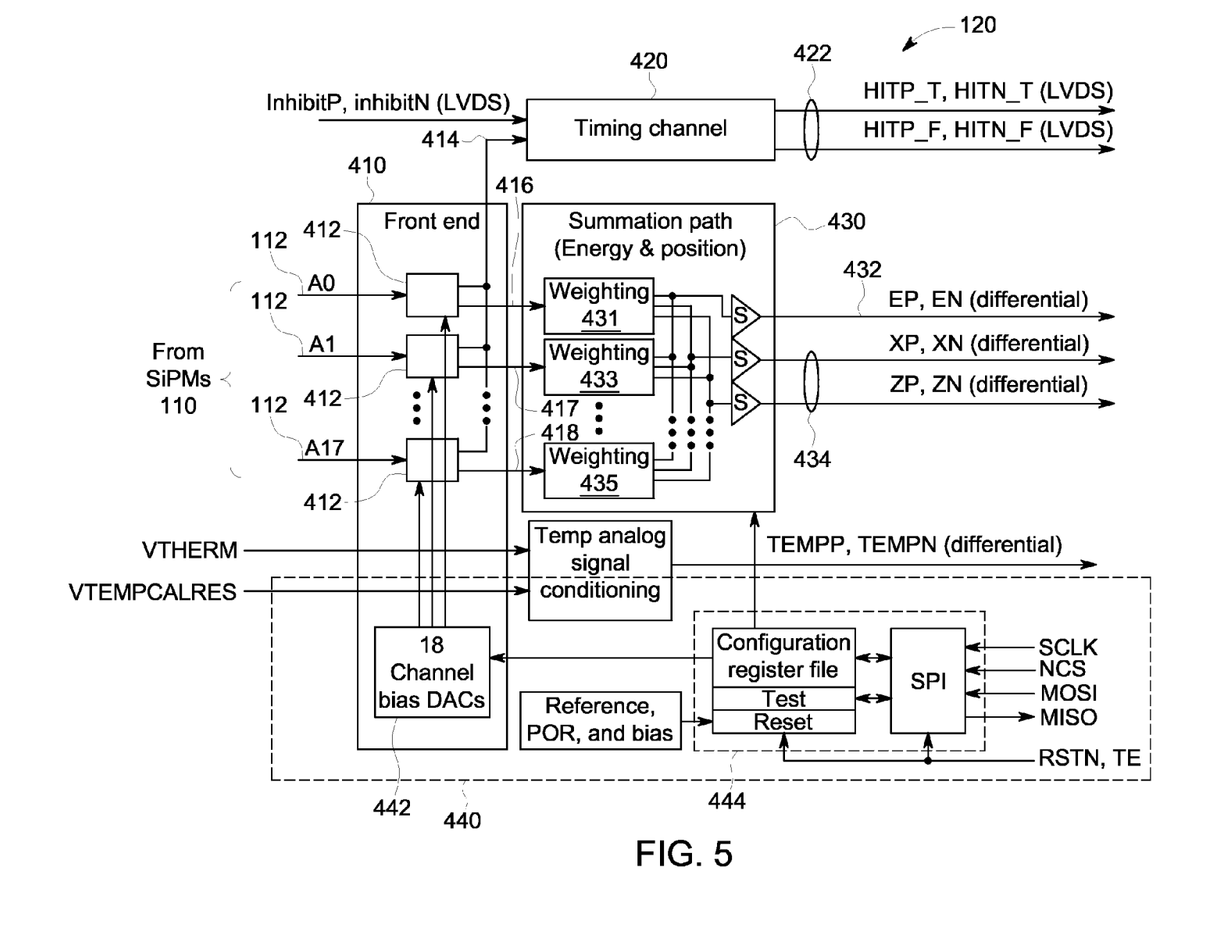
FIG. 5 is a block diagram of one example of an ASIC, in accordance with one embodiment.

FIG. 5 is a block diagram of one example of the ASIC 120 of FIG. 2, according to one embodiment. The ASIC 120 includes a front end circuit 410, a time discriminating circuit 420, an energy discriminating circuit 430 and a bias generation circuit 440. The analog anode outputs 112 of the SiPM devices 110 can be DC coupled to the ASIC front end 410, such as shown in FIG. 5 and described below. The front end circuit 410 can function as a current buffer, and can include one or more amplifiers 412 that have very low input impedance and high bandwidth, which provide high timing resolution and preserve the energy information of the input signals. The front end circuit 410 can amplify and split the signals received from each of the analog anode outputs 112 into two copies using a current mirror; a first copy being output by each of the amplifiers 412, and a second copy being output by each of the amplifiers 412.

The first copy of the amplified signals from each of the amplifiers 412 can be output by the front end circuit 410 on line 414 (e.g., a first channel) as a summation of signals from one or more of the SiPM analog anode outputs 112, which can be used by the time discriminating circuit 420 for generating timing information at outputs 422. The second copy of the amplified signals from each of the amplifiers 412 can be output by the front end circuit 410 on lines 416, 417 or 418 (e.g., a second channel), each corresponding to a respective SiPM 112. The second copy of the amplified signals can be output from the front end circuit 410 to the energy discriminating circuit 430, which can be configured to generated energy and position information at outputs 432 and 434, respectively. For example, the position information may include two-dimensional (e.g., x and z axis) position information provided on separate outputs. The signal to the time discriminating circuit 420 on line 414 may, for example, propagate faster and at a higher bandwidth than the signal to the energy discriminating circuit 430 on lines 416, 417, 418.

In one embodiment, the analog anode output 112 of each SiPM device 110 can be individually biased via a DAC 442 of the ASIC 120 to a certain potential. In this example, where there are 18 SiPMs connected to the front end circuit 410, the DAC 442 may be an 18-channel DAC.

In exemplary embodiments, the energy discriminating circuit 430 can apply weightings 431, 433, 435 to the signals received on lines 416, 417, and 418, respectively. The weighted signals can each have three components: a first component (e.g., an energy output), a second component (e.g., a row output), and a third component (e.g., a column output). Each of the first components can be summed and output on line 432 as a summed energy output. Each of the second components can be summed and each of the third components can be summed. The summed second and third components can be output on line 434 as summed row and column outputs.

Figure 6:
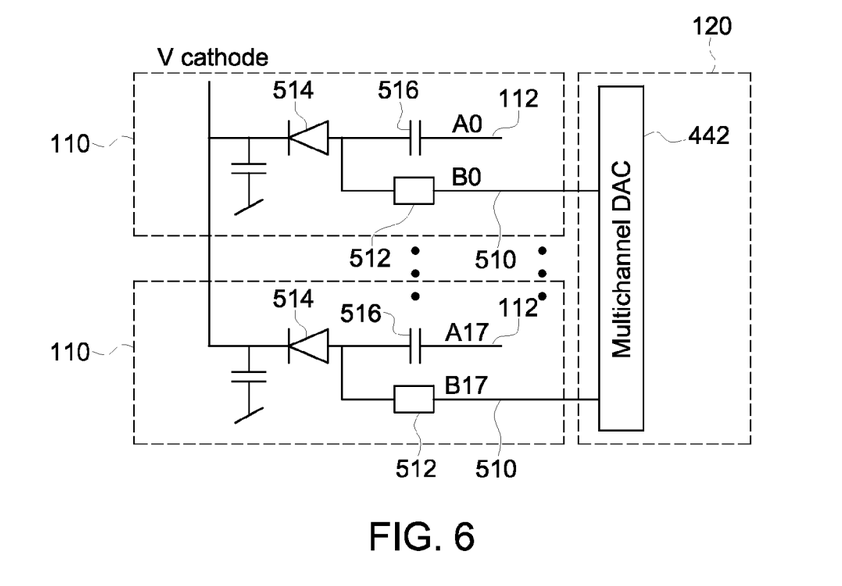
FIG. 6 is a block diagram of one example of a portion of the ASIC of FIG. 5, in accordance with one embodiment.

FIG. 6 is a block diagram of one example of a portion of the ASIC 120 including the DAC 442. The DAC 442 can provide a bias voltage 510 through a resistor 512 to the analog anode outputs 112 of the SiPMs 110. A diode 514 couples the anode output into the front end 410 of FIG. 5 through a capacitor 516.

Referring again to FIG. 5, the front-end 410 may include, for example, eighteen amplifiers that have very low input impedance and high bandwidth and provide a high degree of timing resolution. When needed, each amplifier 412 shown in FIG. 5 can be powered off and disconnected from the time discriminating circuit 420 and the energy discriminating circuit 430 through a controller 442 in the bias generation circuit 440. While powered off, the corresponding anode can be biased to a certain potential to protect the ASIC 120 and to minimize dark current and crosstalk between SiPM devices 110.

In one embodiment, the bandwidth and power level of the front end 410 can be configured through the controller 442. The time discriminating circuit 420 can process a combined signal from corresponding to the outputs 112 of the SiPMs 110 to generate a HIT signal at outputs 422. The energy discriminating circuit 430 can sum a scaled version of the front-end outputs 416, 417, and/or 418 with programmable weights (e.g., weighting 431, 433, 435) to generate energy and position signals at outputs 432 and 434, respectively. In one embodiment, the programmable weights for x and z position coordinates can be identical, which simplifies the system level design. A controller 442 can interface with an external FPGA (not shown) to configure and set the weights.

Figure 7:
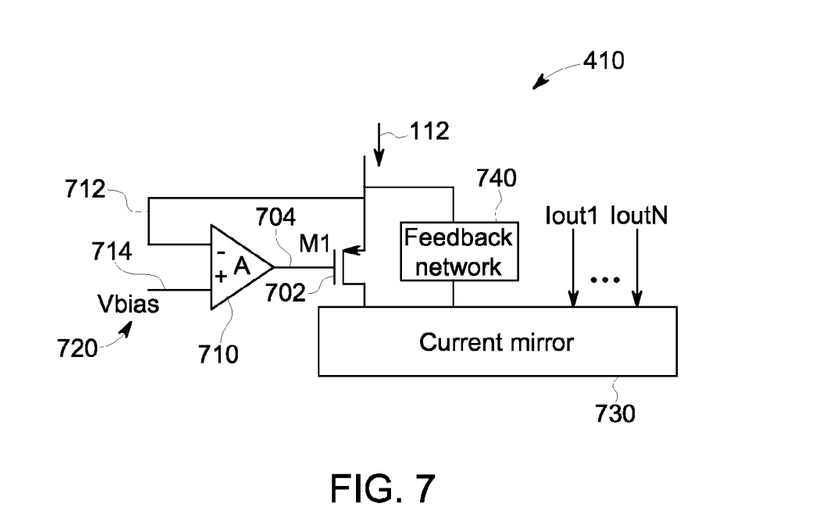
FIG. 7 is a block diagram of one example of a portion of the ASIC of FIG. 5, in accordance with one embodiment.

FIG. 7 depicts one example of the front end circuit 410 of FIG. 5 in further detail, according to an embodiment. The analog anode outputs 112 of the SiPM devices 110 can be directly coupled into the source of a transistor 702. To increase the bandwidth and decrease the input impedance, a negative feedback path can be provided by inserting a voltage amplifier 710 between the anode and the gate 704 of the transistor 702. An inverting input terminal 712 of the amplifier 710 can be coupled directly to the anode 112. A non-inverting terminal 714 of the amplifier 710 can be coupled to a reference voltage $V_{bias}$ 720. The amplifier 710 may, for example, have a high open-loop gain A. Due to the high open loop gain of the negative feedback, the anode voltage can be biased by the negative feedback network at a voltage that is very close to $V_{bias}$. The current flowing into the transistor 702 can be fed into the input branch of a current mirror 730, and create a voltage through its diode connected input transistor of the current mirror. A current feedback network 740 can be inserted between the anode 112 and the current mirror 730 to increase the dynamic range of the front-end current buffer. In some embodiments, N copies of the mirror current with different gains can be used for post-processing, e.g., a copy of the current with a gain of one (1) may be summed into the timing channel for time stamping, and a copy of the current with a gain of one-half may be summed for energy integration and position of crystals.

Having thus described several exemplary embodiments of the invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A multichannel application specific integrated circuit (ASIC) for interfacing with an array of photodetectors in a positron emission tomography (PET) imaging system, the ASIC comprising:
   a front end circuit having a current amplifier and a current mirror, the front end circuit configured to be coupled to the array of photodetectors and to receive a plurality of discrete analog signals there from, wherein the current amplifier comprises;
      an amplifier having an inverting input operably coupled to the front end input, a non-inverting input operably coupled to a bias voltage, and an output; and
      a transistor having a source operably coupled to the front end input, a sink operably coupled to the current mirror, and a gate operably coupled to the output of the amplifier;
   a time discriminating circuit operably coupled to the front end circuit and configured to generate a hit signal based on a combination of the discrete analog signals, the hit signal representing an indication that radiation has been detected by the array of photodetectors;
   a first channel operably coupled between the front end circuit and the time discriminating circuit;
   an energy discriminating circuit operably coupled to the front end circuit and configured to generate a summed energy output signal based on each of the discrete analog signals and summed row and column output signals based on each of the discrete analog signals, the summed energy output signal representing an energy level of the detected radiation in the array of photodetectors, and the summed row and column output signals representing a location of the detected radiation in the array of photodetectors; and
   a plurality of second channels each operably coupled between the front end circuit and the energy discriminating circuit.

2. The ASIC of claim 1, wherein the front end circuit is further configured to:
   transfer the combination of discrete analog signals to the time discriminating circuit using the first channel, and
   transfer each of the discrete analog signals to the energy discriminating circuit using corresponding ones of the plurality of second channels.

3. The ASIC of claim 2, wherein the front end circuit further comprises:
   a front end input operably coupled to an anode of one photodetector in the array of photodetectors;
   a feedback network operably coupled to the front end input and the current mirror;
   a first front end output operably coupled to the current mirror and to the first channel; and
   a second front end output operably coupled a corresponding one of the plurality of second channels.

4. The ASIC of claim 3, wherein the front end circuit is further configured to enable and disable individual photodetectors in the array using a plurality of bias voltages.

5. The ASIC of claim 4, further comprising a biasing circuit operably coupled to the front end circuit and configured to generate the plurality of bias voltages.

6. The ASIC of claim 5, wherein the biasing circuit includes a multichannel digital-to-analog converter.

7. The ASIC of claim 1, wherein the front end circuit is coupled to an anode of each photodetector in the array of photodetectors.

8. The ASIC of claim 1, further comprising a controller operably coupled to the front end circuit and configured to enable and disable individual photodetectors in the array via the front end circuit.

9. The ASIC of claim 1, wherein the array of photodiodes includes an array of Geiger-mode avalanche photodiodes.

10. A method of interfacing with an array of photodetectors in a positron emission tomography (PET) imaging system, the method comprising:
receiving discrete analog signals from each photodetector in the array of photodetectors using a front end circuit, wherein the front end circuit comprises a current amplifier and a current mirror, and wherein the current amplifier comprises an amplifier having an inverting input operably coupled to the front end input, a non-inverting input operably coupled to a bias voltage, and an output and a transistor having a source operably coupled to the front end input, a sink operably coupled to the current mirror, and a gate operably coupled to the output of the amplifier;
generating a hit signal based on a combination of the discrete analog signals using a time discriminating circuit operably coupled to the front end circuit, the hit signal representing an indication that radiation has been detected by the array of photodetectors;
generating a summed energy output signal based on each of the discrete analog signals using an energy discriminating circuit operably coupled to the front end circuit, the summed energy output signal representing an energy level of the detected radiation in the array of photodetectors; and
generating summed row and column output signals based on each of the discrete analog signals using the energy discriminating circuit, the summed row and column output signals representing a location of the detected radiation in the array of photodetectors.

11. The method of claim 10, further comprising:
transferring the combination of discrete analog signals from the front end circuit to the time discriminating circuit using a first channel operably coupled between the front end circuit and the time discriminating circuit; and
transferring each of the discrete analog signals from the front end circuit to the energy discriminating circuit using corresponding ones of a plurality of second channels each operably coupled between the front end circuit and the energy discriminating circuit.

12. The method of claim 10, further comprising enabling and disabling individual photodetectors in the array using at least one of a plurality of bias voltages each corresponding to a respective photodetector.

13. The method of claim 12, further comprising generating the plurality of bias voltages using a biasing circuit operably coupled to the front end circuit.

14. A multichannel application specific integrated circuit (ASIC) for interfacing with an array of photodetectors in a positron emission tomography (PET) imaging system, the ASIC comprising:
a plurality of inputs (1) each having a current amplifier and a current mirror and (2) each configured to be coupled to the array of photodetectors and to receive a plurality of discrete analog signals from each photodetector in the array, wherein the current amplifier comprises:
an amplifier having an inverting input operably coupled to the front end input, a non-inverting input operably coupled to a bias voltage, and an output; and
a transistor having a source operably coupled to the front end input, a sink operably coupled to the current mirror, and a gate operably coupled to the output of the amplifier;
a time discriminating circuit configured to generate a hit signal based on a combination of the discrete analog signals, the hit signal representing an indication that radiation has been detected by the array of photodetectors;
an energy discriminating circuit configured to generate a summed energy output signal based on each of the discrete analog signals and summed row and column output signals based on each of the discrete analog signals, the summed energy output signal representing an energy level of the detected radiation in the array of photodetectors, and the summed row and column output signals representing a location of the detected radiation in the array of photodetectors;
a first channel operably coupled between the plurality of inputs and the time discriminating circuit; and
a plurality of second channels each operably coupled between the plurality of inputs and the energy discriminating circuit.

15. The ASIC of claim 14,
wherein each of the plurality of amplifiers comprises an input operably coupled to an anode of one photodetector in the array of photodetectors, a first output operably coupled to the first channel, and a second output operably coupled to a corresponding one of the plurality of second channels.

16. The ASIC of claim 14, further comprising means for enabling and disabling individual photodetectors in the array.

17. The ASIC of claim 16, wherein the means for enabling and disabling individual photodetectors in the array includes a biasing circuit configured to generate a plurality of bias voltages.

* * * * *